United States Patent

Van Os

[11] Patent Number: 5,494,047
[45] Date of Patent: Feb. 27, 1996

[54] INTRAUTERINE CONTRACEPTIVE DEVICE

[76] Inventor: Willem A. A. Van Os, L'Espéranza, 17, Rue Bosio, 98000, Monaco

[21] Appl. No.: 398,888

[22] Filed: Mar. 6, 1995

[30] Foreign Application Priority Data

Mar. 16, 1994 [NL] Netherlands ............................ 9400410

[51] Int. Cl.$^6$ ...................................................... A61F 6/06
[52] U.S. Cl. ............................................ 128/832; 128/833
[58] Field of Search ...................................... 128/830–841

[56] References Cited

U.S. PATENT DOCUMENTS

| | | |
|---|---|---|
| 3,511,231 | 5/1970 | Robinson . |
| 3,656,483 | 4/1972 | Rudel . |
| 3,820,535 | 6/1974 | Marco . |
| 3,948,254 | 4/1976 | Zaffaroni ................................ 128/833 |
| 4,005,707 | 2/1977 | Moulding, Jr. . |
| 4,014,987 | 3/1977 | Heller .................... 128/832 |
| 4,034,749 | 7/1977 | Von Kesseru .................... 128/833 |
| 4,353,363 | 10/1982 | Sopena Quesada .................... 128/833 |
| 4,678,463 | 7/1987 | Millar .................... 128/832 |
| 4,708,134 | 11/1987 | Wildemeersch . |
| 4,807,610 | 2/1989 | Gainutdinova .................... 128/832 |

FOREIGN PATENT DOCUMENTS

0191747A1  8/1986  European Pat. Off. .
2101533    9/1971  Germany .

Primary Examiner—Michael A. Brown
Attorney, Agent, or Firm—Kane, Dalsimer, Sullivan, Kurucz, Levy, Eisele and Richard

[57] ABSTRACT

The invention relates to an intrauterine contraceptive device having at least two flexible arms. The contraceptive device is provided with at least two almost horizontal arms having solid tips. The arms, are provided at the front and back with cavities in longitudinal direction. The central point of the contraceptive device is provided with a flexible thread, surrounded by a device acting as contraceptive. The active device may consist of copper rings, which rings are retained by a holding means located below the thread. Next to copper rings a flexible tube provided with openings may be used, into which an active contraceptive drug, for instance a hormone preparation, is inserted. An important advantage of the contraceptive device according to the invention is the absence of the vertical stem of the IUD. The arms and the central point of the contraceptive device are made from a flexible synthetic material which is tolerated by the uterus, preferably from polyethylene. The thread is also usually made from a synthetic tolerated by the uterus, preferably from nylon.

7 Claims, 1 Drawing Sheet

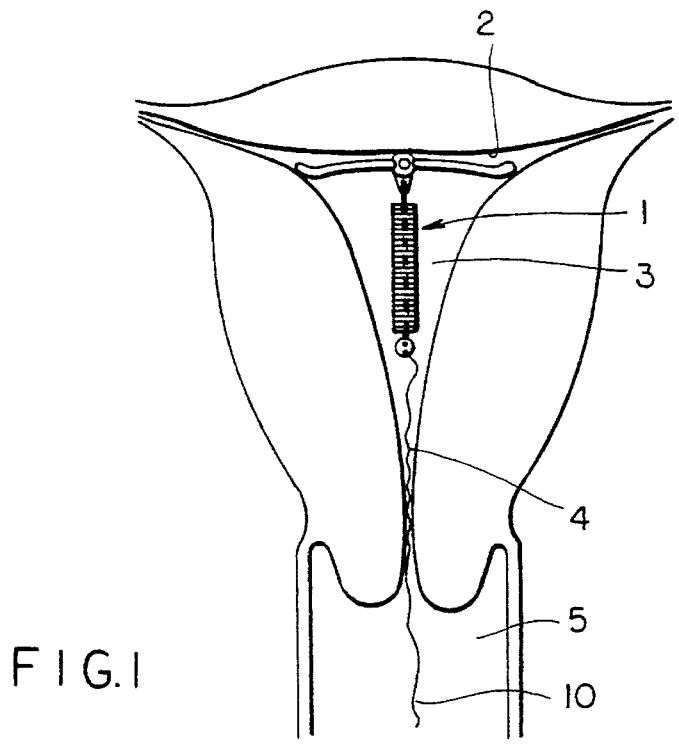
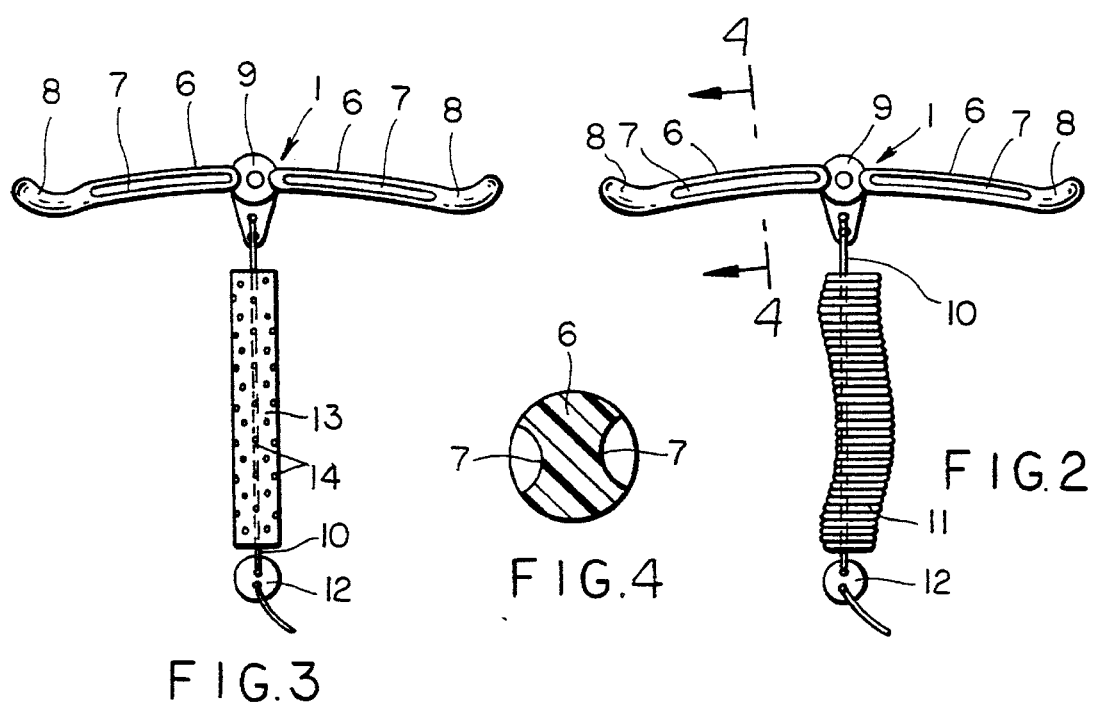

INTRAUTERINE CONTRACEPTIVE DEVICE

BACKGROUND OF THE INVENTION

1. Field of the Invention

The invention relates to an intrauterine contraceptive device comprising at least two flexible arms, extending from a central point.

2. Description of the Related Art

A great variety of mechanical methods of fertility control and of the prevention of pregnancy is known. Is has been known for decades that a foreign object in the virtual cavum uteri is able to prevent conception.

Departing from the basic idea, a large number of different intrauterine contraceptive devices, also called IUDs, have been suggested and applied in practice.

Although these IUDs are effective with regard to controlling or preventing pregnancy, they also have a number of important disadvantages. It has been shown that about 85% of the complaints of side effects of such IUDs relate to bleeding and pain.

There is therefore an ever increasing need for IUDs whereby the above-mentioned disadvantages can be limited to a minimum or completely eliminated. An important advantage would then be that the IUDs can remain much longer inside the uterus with less discomfort for the patient.

At present there is a tendency to give more attention to IUDs with improved properties, as the increase in births in many parts of the world has arrived at a critical stage.

It should be noted that IUDs have already been in use for 30 years, during which 30 years they have been changed many times. The most significant development was the use of copper, which has been proven to have a good anti-fertility effect. Another significant development is the reduction of the size of the IUD's synthetic body because the copper has taken over the anti-fertility activity.

The first IUDs in general use, for instance the Lippes loop, were large filling the uterus. A frequent disadvantage of the large IUDs was that they caused bleeding and pain and therefore often had to be removed in the interim. Research in the sixties and seventies carried out among others by bodies such as the Population Council and the IFRP, has shown that the cause of bleeding and pain was linked to the size of the IUD, with the result that in a great number of cases such large IUDs had to be removed prematurely.

The discovery of copper as anti-fertility means made it possible to make the IUDs much smaller in volume, without reducing the contraceptive effect.

Recent IUD developments point in the direction of extensive size reduction of the IUD in order to further limit or to eliminate bleeding and pain, in order to thus promote the acceptability of the IUDs.

Some of these developments comprise fundally fixed IUDs, whereby the IUD is attached to the uterus fundus. However, these IUDs have the disadvantage associated with the mechanism for attaching the IUD to the fundus. Thus, pain and bleeding can again occur.

The copper intrauterine contraceptive device was developed and resulted in a unique approach in reducing the size of the IUD in order to limit bleeding and pain (the two most occurring reasons why the IUD has to be removed prematurely) to a minimum, while at the same time maintaining a high level of protection against pregnancy.

SUMMARY OF THE INVENTION

It is now the objective of the invention to provide an intrauterine contraceptive device, whereby the above-mentioned disadvantages of bleeding and pain are removed or at any rate limited to a minimum. To this purpose the invention provides an intrauterine contraceptive device comprising at least two arms extending from a central point, characterized in that the tips of the flexible arms, which are solid, are directed toward the fundus, whereby the arms from the central point to about the massive tips along the front and back are hollowed out, while the central point is provided with a flexible thread, surrounded by the means acting as contraceptive, while the thread is provided with a holding device for the means acting as contraceptive.

The IUD according to the invention has the advantage that it can adapt to the physiological changes of the normal uterine cavity. The IUD according to the invention owes this ability to the great flexibility through the applcation of materials which are very resilient, which resilience moreover is enhanced by executing the arms such that they are hollow at the front and back, creating as it were a sort of suction effect, with the result that the arms as it were firmly attach to the uterus walls, fixing the IUD in the uterus without the use of attachment means which would have to be driven into the uterus fundus in order to keep the IUD in place or else the classical vertical stem of the IUD. Moreover, the tips of the arms, which are solid and are directed toward the fundus also allow the IUD to be pressed against the fundus during contractions of the uterus, contributing extra to holding the IUD in place in the uterus. An important aspect of the present IUD is that despite the fact that the IUD according to the invention does not have a vertical stem, good fixation in the uterus is achieved. The stem occurring in a large number of IUDs is also damaging, resulting in an increased chance of pain and bleeding.

The arms and thread of the IUD according to the invention are usually made from a flexible synthetic material which is tolerated by the uterus.

The arms are preferably made from polyethylene and the thread from nylon.

It should be noted that the means acting as contraceptive is preferably copper.

The copper is preferably applied around the thread in the forms of rings, with the result that a high degree of flexibility is obtained because the copper rings can accommodate the movement of the uterus without any damage to the uterus wall, which would occur when using, for instance, a copper spiral.

Good results are also obtained when using as the means acting as contraceptive a flexible synthetic tube tolerated by the uterus, provided with openings containing a usual contraceptive drug. It has been shown that when such a synthetic tube, preferably made of polypropylene, is filled with a usual contraceptically active hormone preparation, good results are also obtained, whereby the disadvantages of the known preparations are eliminated.

The intrauterine contraceptive device according to the invention possesses the following special properties.

In the first place, in the intrauterine contraceptive device according to the invention a vertical stem is absent. The advantage of this is, that the contraceptive device without vertical stem is more compact than with vertical stem, whereby bleeding and pain are limited to a minimum.

On both sides of the horizontal arms cavities are provided, promoting retention of the contraceptive in the uterus. It has, after all, been shown that the insertion of the intrauterine contraceptive device according to the invention allows good adhesion in the uterus walls between the uterus and the arms. The channels on either side of the arms provide as it were a sort of suction effect, causing the uterus walls to lie against the arms, thus preventing downward displacement.

Further, the absence of a vertical synthetic stem prevents endometric damage, which with the known devices is a common cause for bleeding. The decrease in bleeding is coupled to a decrease in the chance of infections in the genital canal. An important advantage of the absence of a vertical stem is that a cervical perforation is avoided.

Further, the arms of the device have a "memory" causing them, as it were, to be pressed against the uterus. This effect, together with the solid tips of each arm being directed toward the fundus, will further prevent downward displacement of the contraceptive device according to the invention.

A by no means unimportant advantage of the copper not being wound around a synthetic stem is the fact, that the length of the copper for a certain copper surface is limited to a minimum. By using a wound copper thread it is also possible to use a thicker thread than was possible up to now, without increasing the maximum diameter of the active part of the contraceptive device according to the invention.

In contrast to other contraceptive devices with a vertical stem, the contraceptive device according to the invention may be inserted by both the buffing as well as the drawing method.

The invention will now be further elucidated by means of the following figures, which show preferred embodiments of the invention without thereby in any way restricting the invention to the same.

BRIEF DESCRIPTION OF THE DRAWINGS

FIG. 1 shows the position of the intrauterine contraceptive device 1 according to the invention in the uterine cavity 3.

FIG. 2 shows a preferred embodiment of the intrauterine contraceptive device 1 according to the invention.

FIG. 3 shows another suitable embodiment according to the invention.

FIG. 4 is a cross section of the horizontal arm 6 along the line V—V shown in FIG. 2.

DESCRIPTION OF THE PREFERRED EMBODIMENTS

FIG. 1 shows clearly that the intrauterine contraceptive device 1 is located adjacent to the fundus of the uterus 2. FIG. 1 further shows the uterine canal 4 and the vagina 5.

FIG. 2 shows in detail a preferred embodiment of the intrauterine contraceptive device 1 according to the invention.

As FIG. 2 clearly shows, the intrauterine contraceptive device 1 according to the invention is provided with two horizontal flexible arms 6, extending from a central point 9. The more or less horizontal arms 6 are provided at the front and back with cavities 7, which cavities extend from the central point 9 over the length of the horizontal arms 6 to about the solid tips 8 of the horizontal arms 6. The solid tips 8 are directed upward. The central point 9 is provided with a flexible thread 10, around which copper rings 11 are placed. These copper rings possess an efficient contraceptive activity. It will be clear that this arrangement of rings is especially flexible, whereby damage to the uterine wall is removed, because the stacked rings can follow the constant movements of the uterus wall.

Below the copper rings the flexible thread 10 is provided with a holding device 12 to arrest the copper rings.

It should be noted that the horizontal arms 6 and the central point 9 are integrally formed from a flexible synthetic material tolerated by the uterus. The synthetic material used is preferably polyethylene, although other flexible synthetic materials tolerated by the uterus may also be used.

The flexible thread 10 is preferably a nylon thread, but it goes without saying that other synthetic threads tolerated by the uterus may also be used.

In practice the synthetic material used is the polymer alathon, which is a polyethylene 21–23% barium sulphate.

It has been shown in practice that a nylon thread having a diameter of 0.24 mm is particularly suitable for use as the flexible thread.

FIG. 3 shows another suitable embodiment of the intrauterine contraceptive device according to the invention, which contraceptive device is provided with almost horizontal arms 6. Just as in FIG. 2, the arms are provided with cavities 7, while the tips 8 of the horizontal arms 6 are solid and directed upward. The means acting as contraceptive used here is a suitable drug of, for instance a hormone preparation, which is lodged in a flexible synthetic tube 13, tolerated by the uterus, provided with openings 14, through which the drug, for example a hormone preparation, is given off in the uterus in order to prevent conception.

The flexible tube is preferably made from polypropylene but other suitable flexible synthetic tubes may also be used.

The synthetic tube 13 provided with openings is so pliable that it can follow the movements of the uterus without damage to the uterus wall.

FIG. 4, finally, shows a cross section of the horizontal arm 6 shown in FIG. 2 along the line V—V.

In this Figure the cavities 7 at the front and back of the horizontal arms 6 are clearly visible.

It should be noted that apart from the preferred embodiments of the intrauterine contraceptive device according to the invention shown in the Figures other versions are possible without deviating from the protective scope of the present invention.

I claim:

1. An intrauterine contraceptive device comprising at least two flexible arms, extending from a central point characterized in that the tips of the flexible arms, which are substantially solid, are massive and directed toward the fundus, whereby the arms from the central point to about the massive tips along the front and back are provided with cavities, while the central point is provided with a flexible thread, surrounded by a means acting as contraceptive, while the thread is provided with a holding device for the means acting as contraceptive.

2. An intrauterine contraceptive device according to claim 1, characterized in that the arms and the thread are made from a synthetic material which is tolerated by the uterus.

3. An intrauterine contraceptive device according to claim 1, characterized in that the arms are made from polyethylene and the thread is made from nylon.

4. An intrauterine contraceptive device as in one of claims 1–3, characterized in that the means acting as contraceptive is copper.

5. An intrauterine contraceptive device according to claim 4, characterized in that the copper is applied in the form of rings around the thread 6. An intrauterine contraceptive device as in one of claims 1–3, characterized in that the means acting as contraceptive is a flexible synthetic tube tolerated by the uterus, provided with openings, containing a usual drug possessing contraceptive activity.

7. An intrauterine contraceptive device according to claim 6, characterized in that the synthetic tube is a polypropylene tube.

* * * * *